(12) United States Patent
Gabriele (10) Patent No.: US 8,287,512 B2
(45) Date of Patent: Oct. 16, 2012

(54) METHOD FOR PRODUCING A CLOSURE ELEMENT FOR ABSORBENT SANITARY PRODUCTS, ABSORBENT SANITARY PRODUCT, AND RESPECTIVE MANUFACTURING METHOD

(75) Inventor: Sablone Gabriele, Montesilvano (IT)

(73) Assignee: Fameccanica.Data S.p.A., Sambuceto di San Giovanni Teatino (Chieti) (IT)

( * ) Notice: Subject to any disclaimer, the term of this patent is extended or adjusted under 35 U.S.C. 154(b) by 586 days.

(21) Appl. No.: 12/518,941

(22) PCT Filed: Nov. 10, 2008

(86) PCT No.: PCT/IB2008/003044
§ 371 (c)(1),
(2), (4) Date: Jun. 12, 2009

(87) PCT Pub. No.: WO2009/063293
PCT Pub. Date: May 22, 2009

(65) Prior Publication Data
US 2010/0016823 A1  Jan. 21, 2010

(30) Foreign Application Priority Data
Nov. 12, 2007  (EP) .................................. 07425711

(51) Int. Cl.
*A61F 13/15* (2006.01)
*A44B 11/25* (2006.01)
*A41H 37/00* (2006.01)

(52) U.S. Cl. ........ 604/389; 604/391; 604/387; 604/394; 24/442; 24/443; 156/227; 156/204; 156/66

(58) Field of Classification Search ................. 604/389, 604/391, 387, 394; 24/442, 443; 156/227, 156/204, 66
See application file for complete search history.

(56) References Cited

U.S. PATENT DOCUMENTS

| 4,704,116 A * | 11/1987 | Enloe | 604/385.27 |
| 6,030,373 A * | 2/2000 | VanGompel et al. | 604/386 |
| 6,575,953 B2 * | 6/2003 | Olson | 604/396 |

\* cited by examiner

Primary Examiner — Jaqueline F. Stephens
(74) Attorney, Agent, or Firm — Nixon & Vanderhye P.C.

(57) ABSTRACT

A method for producing a closure element (10) for disposable pant-like absorbent sanitary products (52) formed by two parts basically symmetrical with respect to a central transverse plane (26), wherein each of said parts is able to form a side panel (76) of an absorbent sanitary product (52). The method comprises the steps of:—folding two continuous strips (22, 24) according to a configuration that comprises at least two parallel branches (30, 40, 44, 46) joined to one another by at least one fold (42, 50, 48); and—fixing permanently respective end branches (30) of said folded strips (30, 40, 44, 46) to a plane base layer (28), with said folded strips (30, 40, 44, 46) basically symmetrical respect to a central plane (26) of said base layer.

24 Claims, 9 Drawing Sheets

METHOD FOR PRODUCING A CLOSURE ELEMENT FOR ABSORBENT SANITARY PRODUCTS, ABSORBENT SANITARY PRODUCT, AND RESPECTIVE MANUFACTURING METHOD

This application is the U.S. national phase of International Application No. PCT/IB2008/003044 filed 10 Nov. 2008 which designated the U.S. and claims priority to European Patent Application No. 07425711.4 filed 12 Nov. 2007, the entire contents of each of which are hereby incorporated by reference.

FIELD OF THE INVENTION

The present invention relates to absorbent sanitary products and has been developed with particular attention paid to its possible application to absorbent sanitary products that can be worn as pants. A typical example of absorbent sanitary products of this type is represented by the so-called training pants.

DESCRIPTION OF THE PRIOR ART

US-A-2002/0111596 (Fletcher et al.), discloses a pant-like absorbent garment having removable side panels that are releasable and refastenable, in such a way that the absorbent garment can be opened and closed on its front side or on its dorsal side, both on the right and on the left. The removable side panels can be re-used with a disposable absorbent section of the garment and are made of partially or completely elasticized material. Each side panel is formed by a strip folded so as to present four parallel branches, with two central branches joined to one another by a fold and with each of the two central branches connected by a respective fold to a respective outer branch. The two outer branches are fixed to respective micro-hook closure devices.

In this known solution, each side panel is an autonomous component. Consequently, the automatic machines for producing garments of this type must apply two distinct side panels for each garment. On the production line, the side panels must be alternatively applied in directions opposite to one another, which complicates considerably the device that carries out application of the side panels.

EP-A-1523968 in the name of the present applicant discloses a closure element formed by two symmetrical parts, which, after application to a continuous chain of semifinished products, is cut together with the chain of semifinished products in a region corresponding to the plane of symmetry so as to form two side closures of two adjacent products. This solution enables application of just one closure element for each product, and all the closure elements are applied with the same orientation. The closure element has a general omega-shaped configuration, with two substantially C-shaped side parts joined by respective folds to a rectilinear central stretch. The main drawback of this solution is represented by the fact that it is problematical to make with automatic machines at high speed the folds that join the two side parts to the central stretch.

The European patent application No. 07425518 (not yet published at the date of filing of the present application) discloses a closure element with elastic side panels formed by two symmetrical side parts, obtained by folding a continuous strip. Each of the two symmetrical parts comprises four parallel branches, with the adjacent branches joined to one another by respective folds. The end branches of the two side parts are joined to a base branch by means of respective folds. Also with this solution, it is problematical to make with high-speed automatic machines the folds that join the two side parts to the base stretch.

OBJECT AND SUMMARY OF THE INVENTION

The object of the solution described herein is to overcome the drawbacks of the prior art.

According to the solution described herein, said object is achieved by a method for producing a closure element having the characteristics forming the subject of claim 1 and by a method for producing sanitary products having the characteristics forming the subject of claim 12. The solution described herein moreover regards a sanitary product having the characteristics forming the subject of claim 11.

The claims form an integral part of the technical teaching provided herein.

As will emerge clearly in the course of the ensuing detailed description, the solution described herein enables a simplification in the production of closure elements for pant-like sanitary products in so far as it eliminates the need to make the most problematical folds.

BRIEF DESCRIPTION OF THE ANNEXED DRAWINGS

The present solution will now be described in detail with reference to the attached drawings, which are provided purely by way of non-limiting example and in which.

DETAILED DESCRIPTION OF EXAMPLES OF EMBODIMENT

Figure 1:
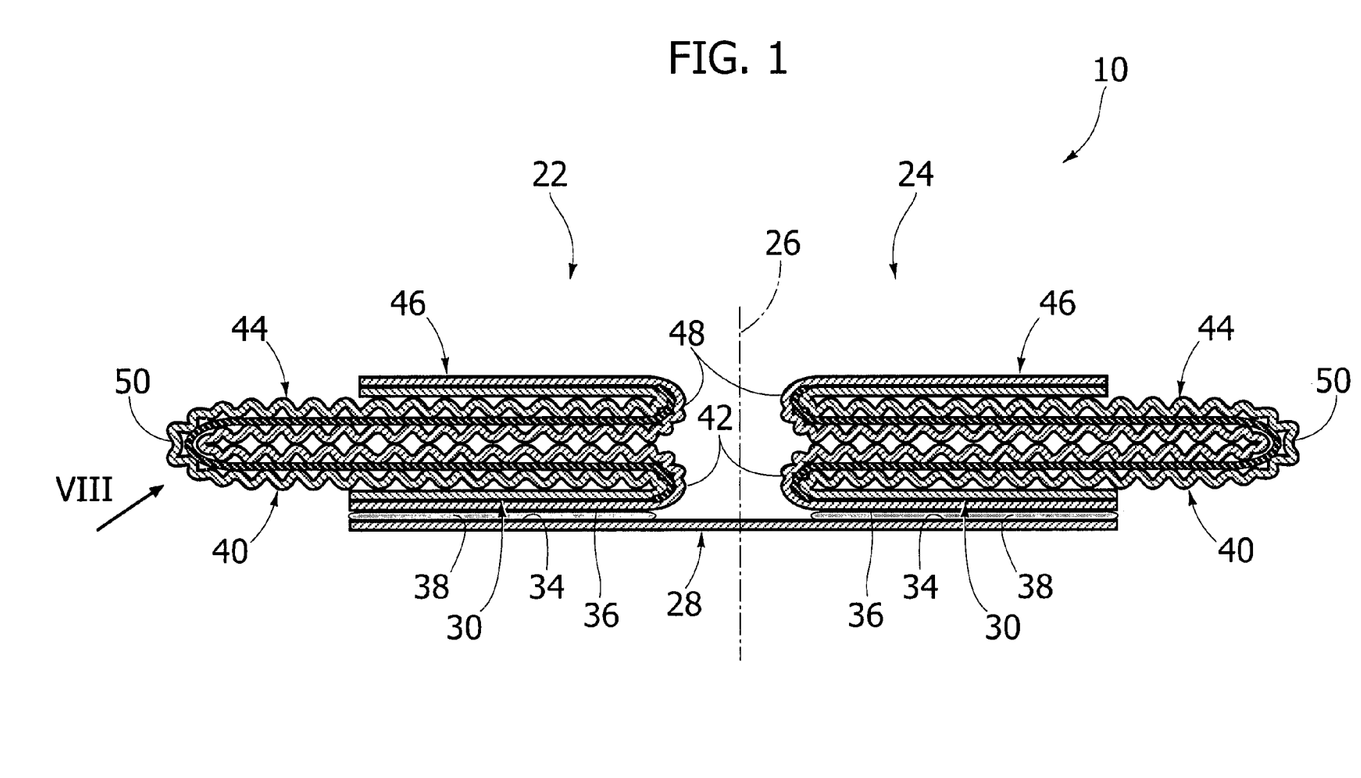
FIG. 1 is a cross section of a closure element with elastic side panels according to the solution described herein.

With reference to FIG. 1, designated by 10 is a closure element with elastic side panels for pant-like absorbent sanitary products.

Figure 2:
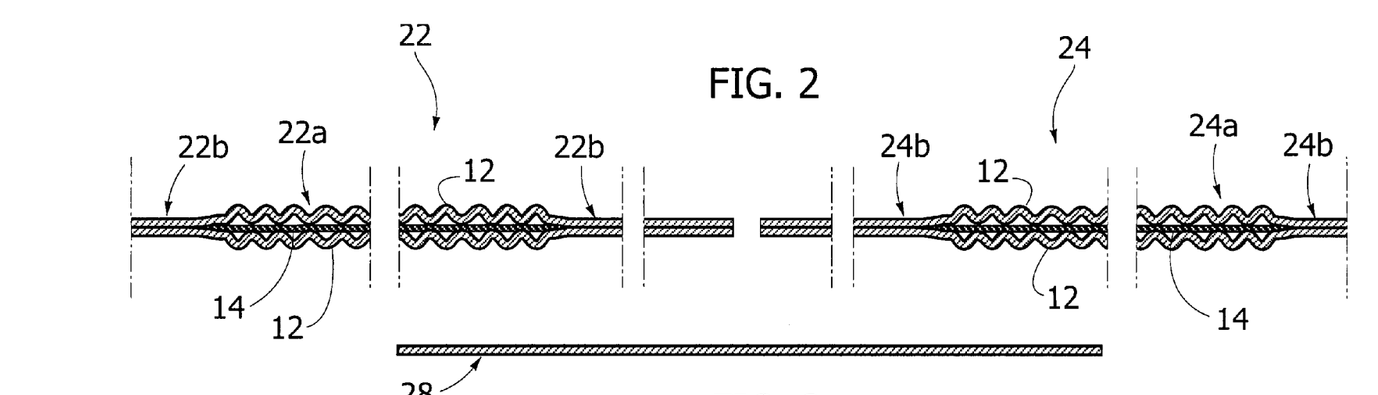
FIG. 2 is a cross section illustrating the components used for producing the closure element of FIG. 1.
Figure 3:
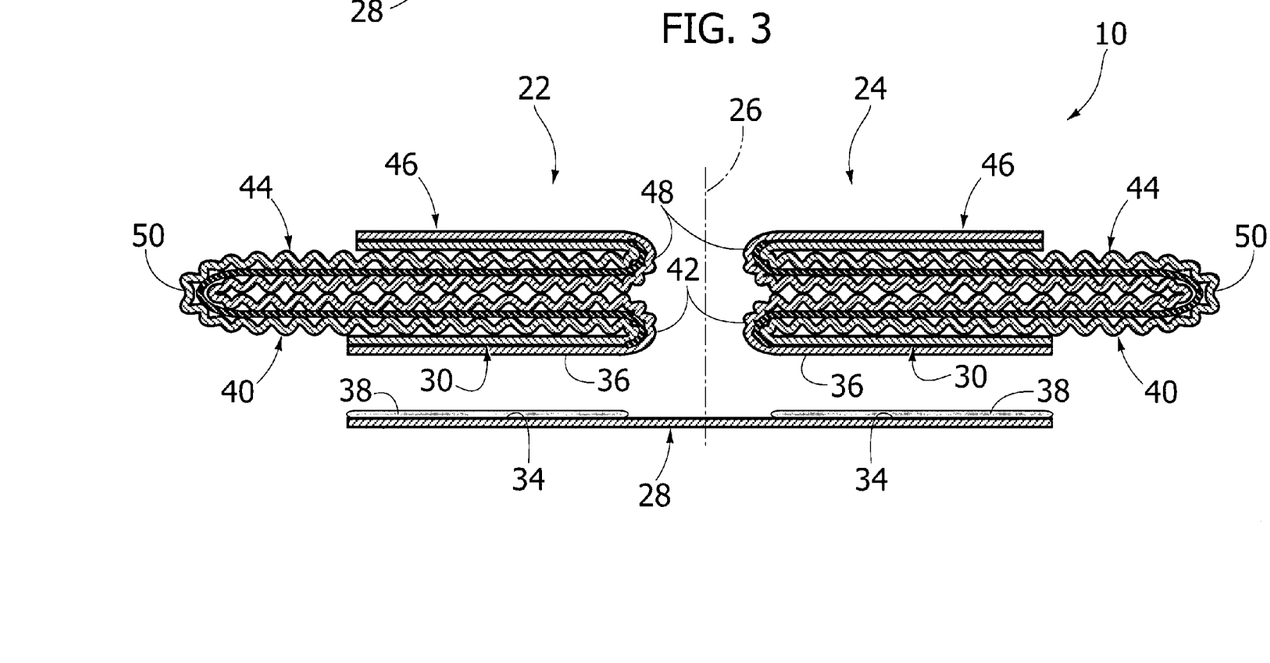
FIG. 3 is a schematic cross section illustrating a step of the method for producing closure elements according to the solution described herein.

With reference to FIGS. 2 and 3, the closure elements 10 are obtained starting from three continuous longitudinal strips 22, 24 and 28 separated from one another.

The strips 22, 24 are substantially identical to one another and each of them comprises a central stretch 22a, 24a made of elasticized material, and two side stretches 22b, 24b made of non-elasticized material. The strips 22, 24 and 28 extend in a continuous way in a longitudinal direction orthogonal to the direction of representation of FIG. 2.

Preferably, each of the strips 22, 24 comprises two layers of non-woven fabric 12 coupled to one another and between which, applied in the elasticized stretches 22a, 24a are non-pretensioned elastic films 14, of a commercially available type, which become elastic after mechanical activation of the layers of non-woven fabric 12. Alternatively, the elasticized stretches 22a, 24a can be obtained by means of pre-tensioned elastic threads (for example, made of the material marketed under the trademark Lycra® by Dupont) or else elastic films. The aforesaid elastications are made according to technologies in themselves known. In the absence of a force in the longitudinal direction, in the stretches of elasticized material 22a, 24a the layers of non-woven fabric 12 can assume an undulated shape as represented in FIG. 2. Under the action of a transverse force, the stretches of elasticized material 22a, 24a lengthen, and the layers of non-woven fabric 12 distend.

The third strip 28 is constituted by a continuous plane web made of non-elasticized material, preferably formed by a single layer of non-woven fabric.

Each of the strips 22, 24 undergoes three folds at 180° about axes parallel to the longitudinal extension of the strips. Following upon said folds, each of the strips 22, 24 assumes the conformation illustrated in FIG. 3. One fold is made substantially at the centre of the elasticized stretch 22a, 24a and another two folds are made in a region corresponding to the area of transition between the central elasticized stretch 22a, 24a and the non-elasticized side stretches 22b, 24b.

At the end of the folding operation, each strip 22, 24 comprises four parallel branches. More precisely, each folded strip comprises a first branch 30 made of non-elasticized material, a second branch 40 made of elasticized material connected to a respective end of the first branch 30 by means of a first fold 42, a third branch 44 made of elasticized material connected to a respective end of the second branch 40 by means of a second fold 50, and a fourth branch 46 made of non-elasticized material connected to a respective end of the third branch 44 by means of a third fold 48.

After the strips 22, 24 are folded, they are fixed in a permanent way to the third strip 28, which remains plane. With reference to FIG. 3, the two folded strips 22, 24 are set symmetrical to one another with respect to a central longitudinal plane 26 of the third strip 28. The third strip 28 and the first branches 30 have respective mutually facing surfaces 34, 36, which are fixed to one another permanently, for example by means of respective layers of glue 38 or by means of sealing.

After the folded strips 22, 24 have been fixed to the third strip 28, a continuous longitudinal web is obtained having in cross section the shape illustrated in FIG. 1. The continuous web is cut in a transverse direction into stretches of constant length to form successive closure elements 10.

In each closure element 10, the third strip 28 forms a base layer that joins the two folded strips 22, 24 to one another. The first and third folds 42, 48 are set at a distance with respect to the central longitudinal plane 26 so as to leave an empty space around the central plane 26 in a region corresponding to a central area of the base layer 28. The second branches 40 and the third branches 44 extend in a lateral direction towards the outside beyond the external side ends of the first branches 30 and fourth branches 46. Preferably, the first branches 30 and the fourth branches 46 have substantially the same length.

Figure 4:
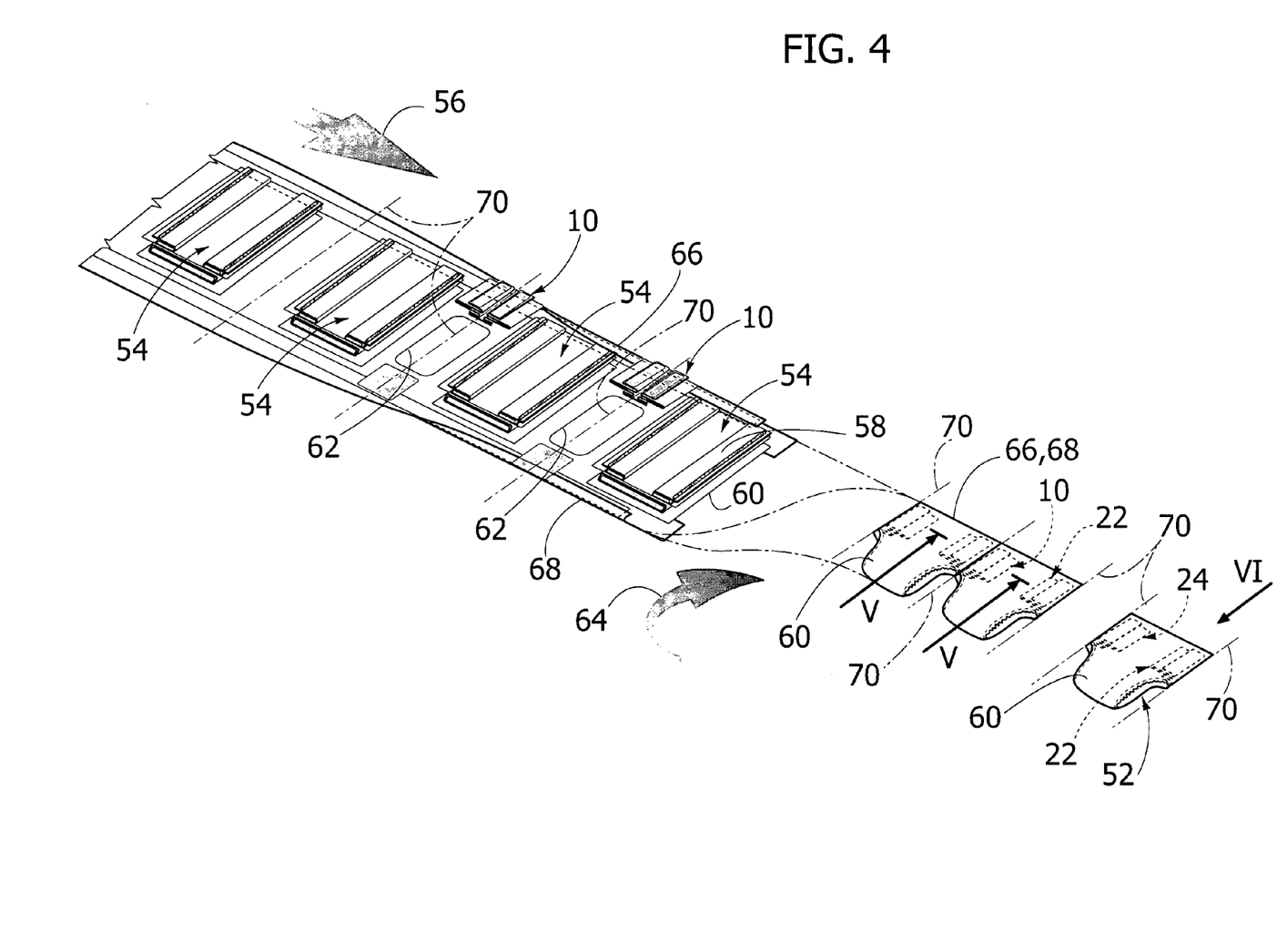
FIG. 4 is a schematic perspective view illustrating a method for producing absorbent sanitary products, using closure elements according to the solution described herein.

FIG. 4 schematically shows a method for producing pant-like absorbent sanitary products. One of said products is designated by 52 in FIG. 4. The products 52 are obtained starting from a continuous chain of semifinished products 54 that advances in the longitudinal direction indicated by the arrow 56. The chain of semifinished products 54 is formed according to criteria in themselves known. Typically, the chain of semifinished products 54 has a sandwich structure comprising a topsheet 58 and a backsheet 60, set between which is an absorbent layer. The chain of semifinished products 54 is provided with openings 62, set at a distance from one another in a longitudinal direction, which form the holes for the legs of the products 52. FIG. 4 illustrates a sequence of production of products 52 of the type referred to as cross-direction. In machines of this type, the continuous longitudinal chain of semifinished products 54 is subjected to a fold indicated by the arrow 64, following upon which two opposite longitudinal edges 66, 68 of the chain of semifinished products 54 are superimposed on one another.

Figure 10:
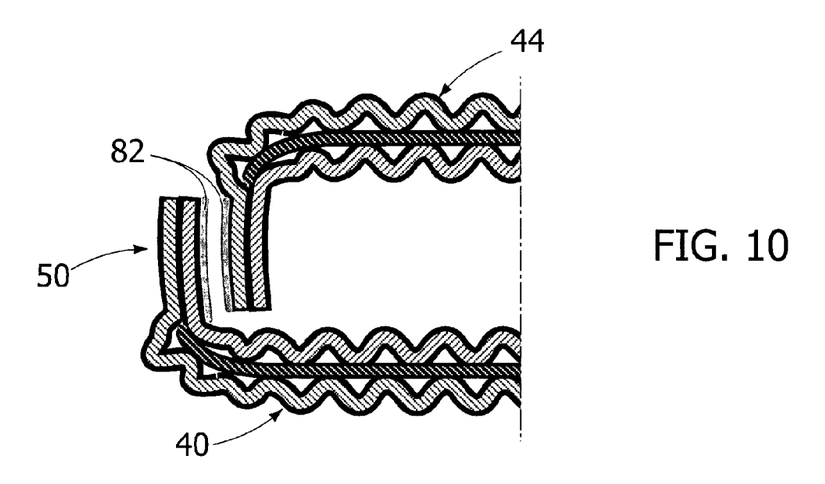

Before making the fold of the continuous chain of semifinished products 54 in the direction indicated by the arrow 64, the closure elements 10 are applied to the chain 54 in positions set at a distance from one another in the longitudinal direction. The closure elements 10 are applied in such a way that the central plane 26 of each element 10 is substantially aligned to a transverse demarcation line 70 between each pair of adjacent semifinished products 54. The elements of FIG. 10 are applied on the topsheet 58 in a region corresponding to one of the two longitudinal edges 66, 68 (to the longitudinal edge 66 in the representation of FIG. 3). Just one closure element 10 is applied in an area corresponding to each demarcation line 70, and all the closure elements 10 are applied with the same orientation. The closure elements 10 are applied to the chain of semifinished products 54 by gluing, sealing, or micro-hook closure devices. In the example illustrated in FIG. 3, the base layer 28 of each closure element 10 is glued to the topsheet 58 in an area corresponding to the longitudinal edge 66. Following upon folding in the direction indicated by the arrow 64, the topsheet 58 adjacent to the opposite edge 68 is glued to the fourth branches 46 of each closure element 10.

The closure elements 10 could also be applied in an opposite direction with respect to the ones of FIG. 3, i.e., with the fourth branches 46 glued to the topsheet 58 in an area corresponding to the edge 66 and with the opposite edge 68 that is glued to the base layer 28 of each element 10 following upon folding of the chain of semifinished products 54 in the direction indicated by the arrow 64.

Figure 5:
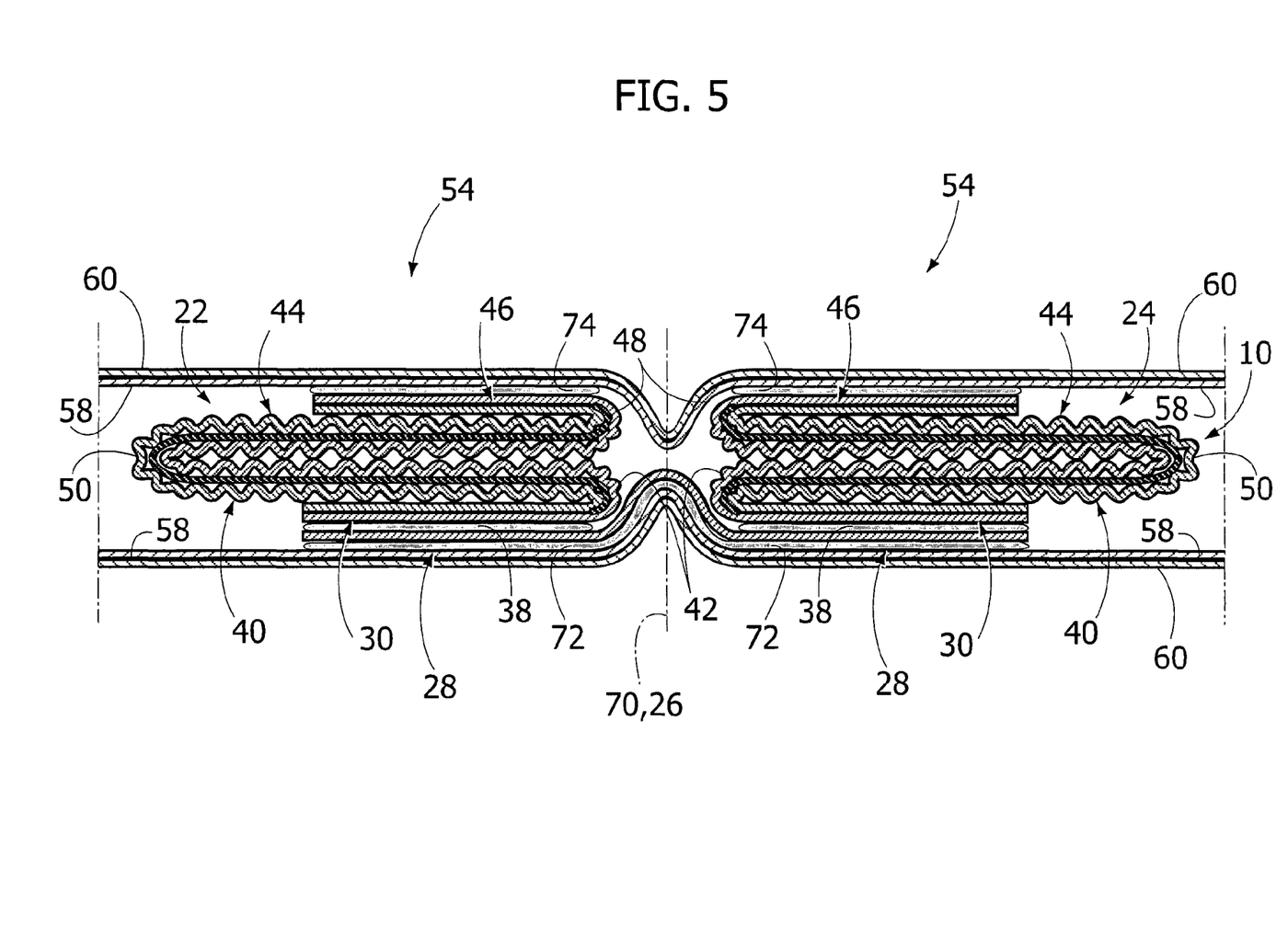
FIG. 5 is a cross section at a larger scale according to the line V-V of FIG. 4.

After folding of the chain of semifinished products 54 according to the arrow 64, the area of connection between each pair of adjacent semifinished products 54 assumes the form illustrated in FIG. 5. The demarcation line 70 between two adjacent semifinished products 54 is positioned substantially in an area corresponding to the central plane 26 of each closure element 10. The two folded strips 22, 24 of each closure element 10 are set on opposite sides with respect to the demarcation line 70. The base layer 28 of the closure element 10 is fixed to the topsheet 58 of the front or dorsal side of the semifinished product 54 by means of a layer of glue 72, and the fourth branches 46 of the closure element 10 are fixed by means of layers of glue 74 to the topsheet 58 of the opposite side (dorsal or front) of the semifinished products 54.

In this condition, a transverse cut is made in the demarcation line 70 between each pair of adjacent semifinished products 54. With this operation the topsheet 58 and the backsheet 60 of the dorsal side, the base layer 28 of the closure element 10, and the topsheet 58 and the backsheet 60 of the front side are cut. Following upon cutting, the finished products 52 are obtained, one of which is illustrated on the right-hand side of FIG. 4.

Figure 6:
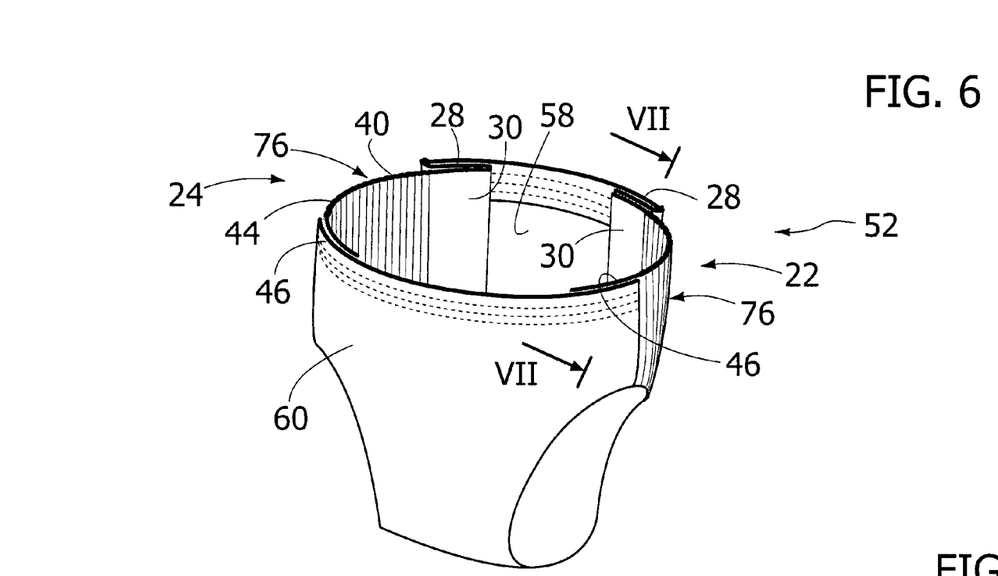
FIG. 6 is a schematic perspective view illustrating a finished sanitary product indicated by the arrow VI in FIG. 3 in conditions of use.
Figure 7:
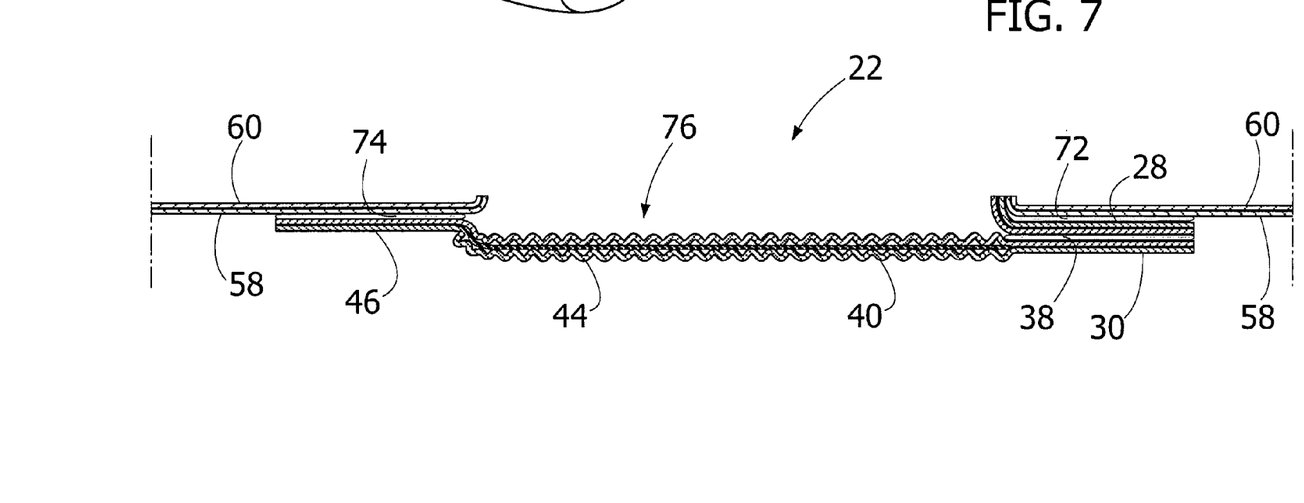
FIG. 7 is a cross section at a larger scale according to the line VII-VII of FIG. 5.

FIG. 6 illustrates an absorbent sanitary product obtained with the method described previously in the condition of use. The product 52 is provided with two side panels 76 made of elasticized material, formed by the elasticized stretch of strip 22, 24 of a closure element 10. As may be noted in particular in FIG. 7, in the stretches corresponding to the layers of glue 38, 74 the material is not elasticized. This enables reduction in the thickness of the areas of connection and improvement of the adhesive connection. The area of elasticized material extends only in a region corresponding to the areas without glue, and this enables complete exploitation of the elasticized part.

In the embodiment so far described, a pant-like product 52 with elasticized sides is obtained.

Figure 8:
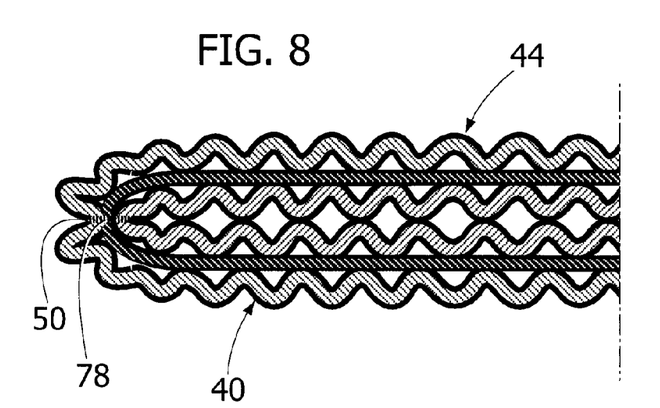
FIGS. 8, 9 and 10 are enlarged details of the part indicated by the arrow VIII in FIG. 1, illustrating different variants.

According to a first variant illustrated in FIG. 8, each closure element 10 can be provided with lines of preferential tearing 78 positioned in a region corresponding to the second folds 50. In this way, each side panel 56 is provided in a central position with a line of tear for removal of the product 52. Alternatively, the two branches 40, 44 could be connected to one another by means of mechanical sealing, heat sealing, ultrasound sealing, etc.

Figure 9:
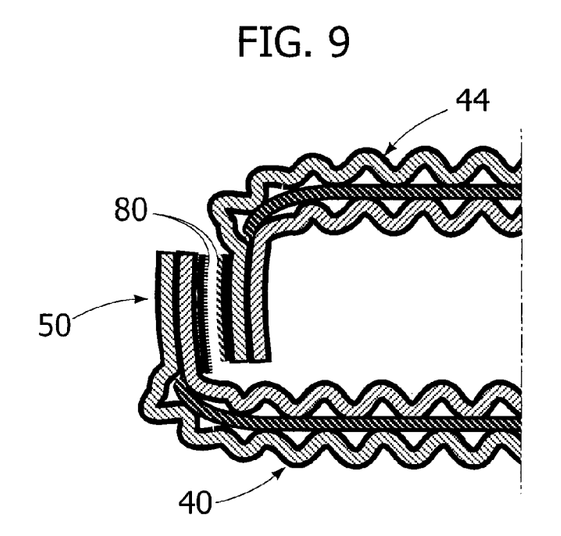

According to a further advantageous characteristic of the solution described herein, the product 52 can be of a type releasable and refastenable. As is illustrated in FIG. 9, to afford the possibility of releasing and refastening the product 52, a micro-hook closure device 80 can be provided in the area of connection between the second branches 40 and the third branches 44 of each closure element 10. The micro-hook closure device 80 extends at the centre of each side panel 76 and enables releasing, inspection, and possibly refastening of the product 52 whilst this is worn.

As an alternative to the use of a micro-hook closure device 80, illustrated in FIG. 10, is the use of a layer of glue 82 of a "pressure sensitive" type, which connects together in such a releasable and refastenable way the ends of the second branches 40 and third branches 44 of each closure element 10. The layer of glue 82 enables releasing and refastening of each side panel 76 in a way similar to a micro-hook closure.

Figure 11:
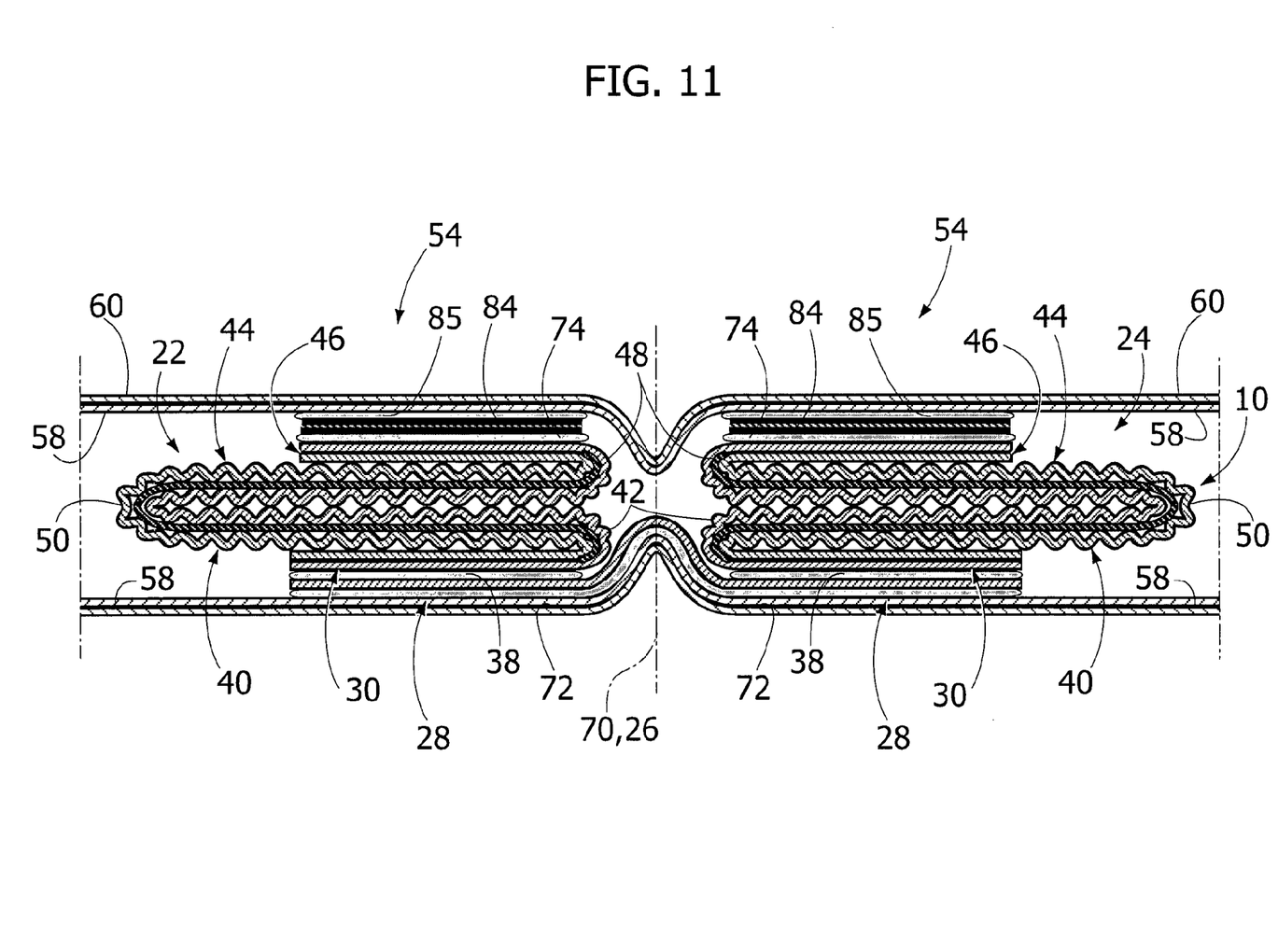
FIG. 11 is a cross section corresponding to that of FIG. 5 and illustrating a variant of the solution described herein.

As further alternative for providing a releasable and refastenable product, the solution illustrated in FIG. 11 can be adopted. In this case, the fourth branches 46 of each closure element 10 are connected to the corresponding topsheet 58 by means of micro-hook closure devices 84. Each micro-hook closure device 84 is fixed to the branch 46 and to the topsheet 58 by means of respective layers of glue 74, 85. The closure device 84 can be provided on the front side or on the dorsal side of the product. The micro-hook closure device 84 enables also an adjustment of the diameter of the waist of the product 52. Alternatively, the micro-hook closure device 84 can be applied to the base layer 28. As further alternative, the base layer 28 and/or the fourth branches 46 can be fixed to the respective topsheet 58 by means of layers of glue of a type that can be opened and reclosed (pressure-sensitive glue).

FIGS. 12 to 16 show a simplified embodiment of the closure element 10. The items corresponding to the ones described previously are designated by the same reference numbers.

Figure 12:
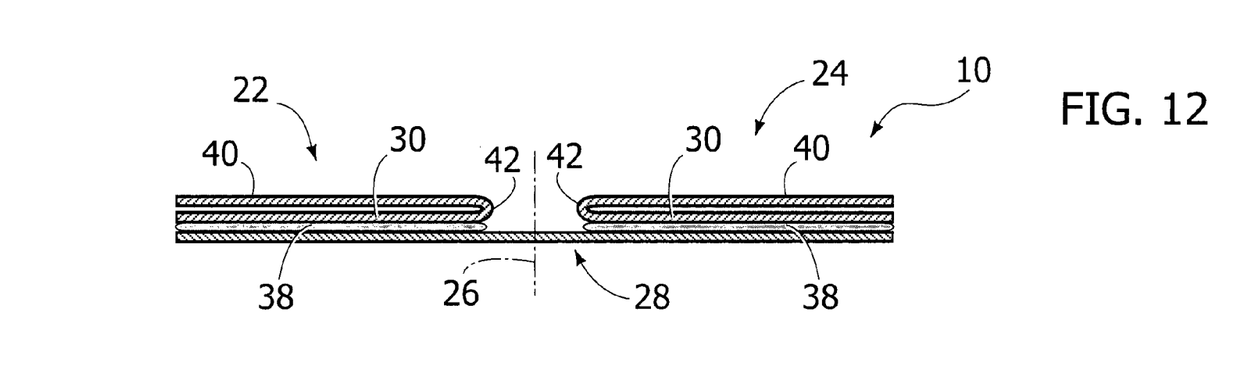
FIG. 12 is a cross section illustrating a simplified embodiment of a closure element according to the solution described herein.

FIG. 12 shows a closure element 10 formed by two strips 22, 24 made of non-elasticized material, fixed to a base layer 28 also made of non-elasticized material. Each of the two strips is folded substantially to form a C and has only a first branch 30 and a second branch 40, joined to one another by a fold 42. After folding of the strips 22, 24, the first branch 30 of each strip 22, 24 is fixed in a permanent way to the third strip 28 by means of a layer of glue 38 or by sealing, in a way similar to what has been described previously.

Figure 13:
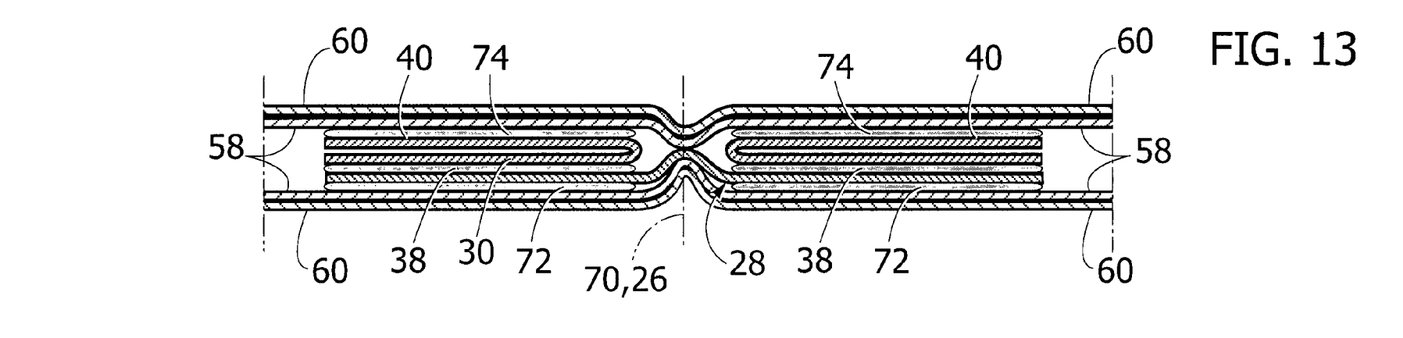
FIG. 13 is a cross section corresponding to FIG. 5, illustrating the closure element of FIG. 12 after application to a chain of semifinished products.
Figure 14:
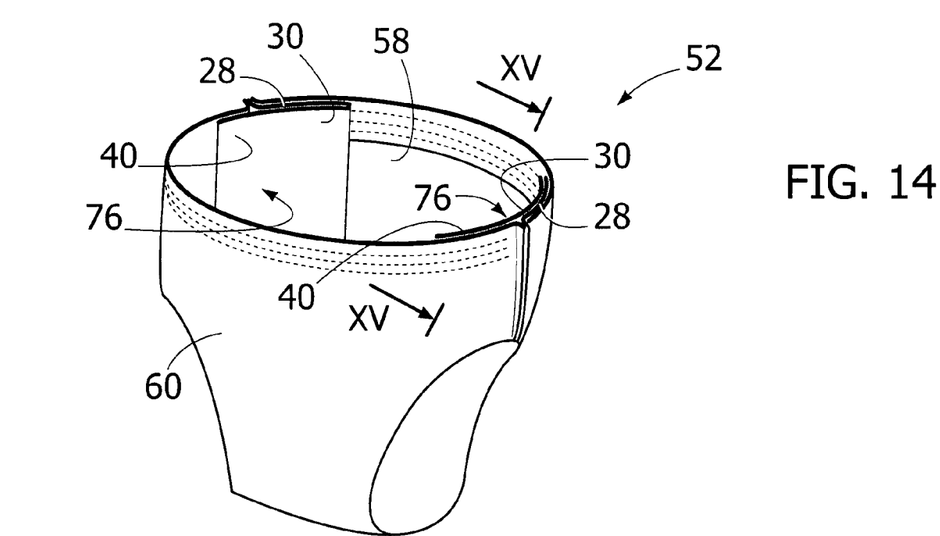
FIG. 14 is a perspective view of an absorbent sanitary product using closure elements according to FIG. 12.
Figure 15:
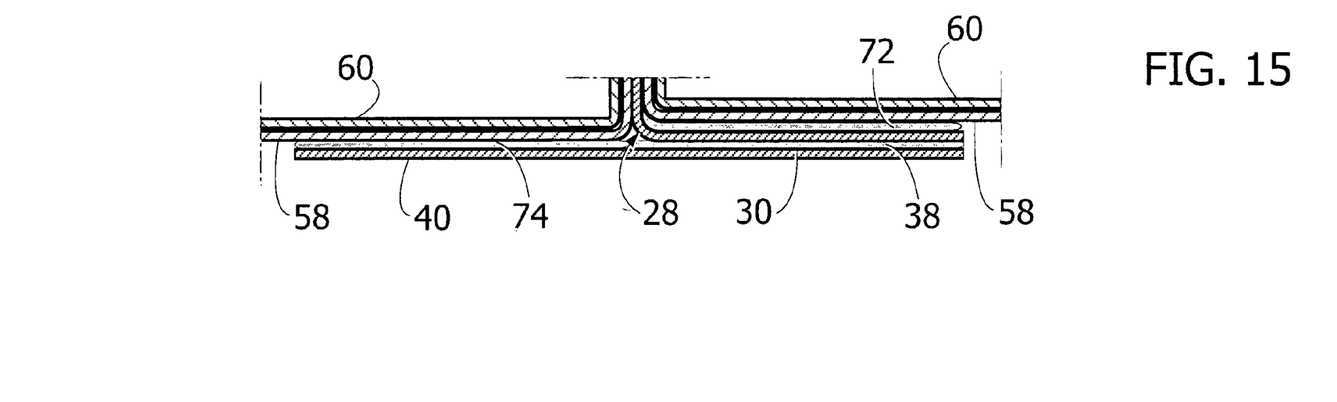
FIG. 15 is a cross section at a larger scale according to the line XV-XV of FIG. 14.

FIG. 13 shows the fixing element 10 of FIG. 12 after its application to a continuous chain of semifinished products, according to the modalities described previously with reference to FIG. 4.

In a way altogether corresponding to what has been described with reference to the previous embodiment, after cutting in the demarcation lines 70 between the adjacent semifinished products, the finished products 52 are obtained, one of which is shown in FIG. 3 in the position of use. The finished product 52, unlike the version described previously, is not provided with elasticized sides but only with two non-elasticized side panels 76, which join the opposite edges of the product together along the waist line.

Figure 16:
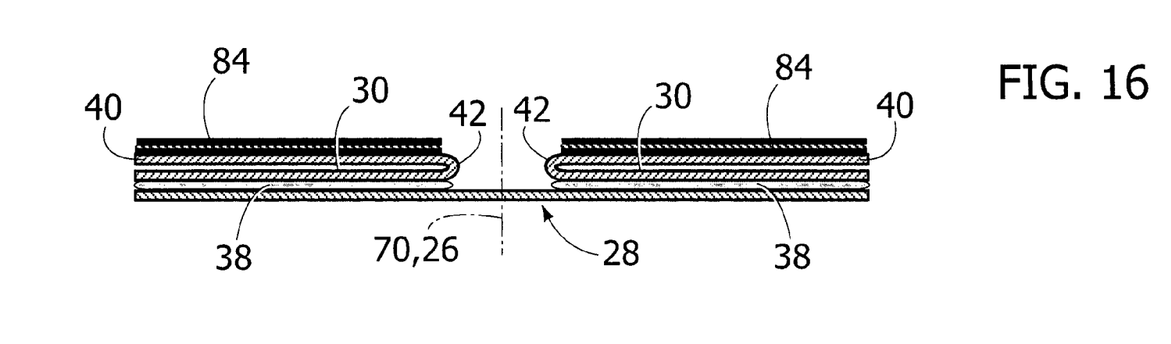
FIG. 16 is a cross section illustrating a variant of the closure element of FIG. 11.

With reference to FIG. 16, the closure element 10 of this second embodiment could be provided with a micro-hook closure device 84 applied on the outer side of the branches 40. In this way, the product 52 becomes of a type releasable and refastenable.

The closure element 10 of this second embodiment could be provided with a line of preferential tearing or else with a closure that can be opened and reclosed in a region corresponding to the fold 42 between the two branches 30, 40, in a way similar to what is illustrated in FIGS. 8 to 10 of the embodiment described previously.

The invention claimed is:

1. A method for producing a closure element for disposable pant-like absorbent sanitary products, said element being formed by two parts basically symmetrical with respect to a central transverse plane, each of said parts being able to form a side panel of an absorbent sanitary product, each of said symmetrical parts comprising at least two parallel branches joined by at least one fold, wherein the method comprises the steps of:
  folding two continuous strips according to a configuration that comprises at least two parallel branches joined to one another by at least one fold; and
  fixing in a permanent way respective end branches of said folded strips to a plane base layer, with said folded strips basically symmetrical with respect to a central plane of said base layer, and
  wherein said plane base layer is formed by a single layer of non-woven fabric.

2. The method according to claim 1, wherein each of said continuous strips comprises a central elasticized stretch and two side stretches made of non-elasticized material, and in that said base layer is made of non-elasticized material.

3. The method according to claim 1, wherein said continuous strips and said base layer are made of non-elasticized material.

4. The method according to claim 1, wherein said continuous strips are folded so as to form four parallel branches, with the adjacent branches joined to one another by folds, wherein two central adjacent branches are made of elasticized material and two end branches are made of non-elasticized material.

5. The method according to claim 4, wherein a line of preferential tearing is provided in a region corresponding to the fold between said central branches.

6. The method according to claim 4, wherein the two central branches are connected to one another by means of a releasable and refastenable closure device.

7. The method according to claim 4, wherein micro-hook closure devices are fixed to the branches of said strips opposite to said base layer.

8. The method according to claim 1, wherein said continuous strips are folded according to a C-shaped configuration.

9. The method according to claim 8, wherein a line of preferential tearing is provided in a region corresponding to the fold between said branches folded to form a C.

10. The method according to claim 8, wherein said branches folded to form a C are connected to one another by means of a releasable and refastenable closure device.

11. A disposable pant-like absorbent sanitary product, comprising an absorbent structure and two side panels, wherein each of said side panels is formed by one half of a closure element obtained by means of a method according to claim 1.

12. A method for producing disposable pant-like absorbent sanitary products, comprising the steps of:
forming a continuous longitudinal chain of semifinished products having a first longitudinal edge and a second longitudinal edge opposite to one another;
forming closure elements each including a base layer and two parts symmetrical with respect to a central plane of said base layer;
fixing said closure elements to said chain of semifinished products in positions set at a distance from one another in a longitudinal direction at a first longitudinal edge of the chain of semifinished products, with the central plane of each closure element set in an area corresponding to a demarcation line between each pair of adjacent semifinished products;
folding said chain of semifinished products so as to superimpose said opposite longitudinal edges on one another and fix the second longitudinal edge to said closure elements; and
cutting said chain of semifinished products and said closure elements along said demarcation line in such a way that following upon cutting of the two symmetrical parts of each closure element respective side panels of two successive products will be formed,
wherein the step of formation of said closure elements comprises the steps of:
folding two continuous strips according to a configuration that comprises at least two parallel branches joined to one another by at least one fold; and
fixing permanently respective end branches of said folded strips to a plane base layer, with said folded strips basically symmetrical with respect to a central plane of said base layer.

13. The method according to claim 12, wherein each closure element is fixed to the first longitudinal edge of the continuous chain of semifinished products by means of a system chosen between: sealing, layer of glue, and micro-hook closure device.

14. The method according to claim 12, wherein the second longitudinal edge of the continuous chain of semifinished products is fixed to each closure element by means of a system chosen between: sealing, layer of glue, and micro-hook closure device.

15. A method for producing a closure element for disposable pant-like absorbent sanitary products, said element being formed by two parts basically symmetrical with respect to a central transverse plane, each of said parts being able to form a side panel of an absorbent sanitary product, each of said symmetrical parts comprising at least two parallel branches joined by at least one fold, wherein the method comprises the steps of:
folding two continuous strips according to a configuration that comprises at least two parallel branches joined to one another by at least one fold; and
fixing in a permanent way respective end branches of said folded strips to a plane base layer, with said folded strips basically symmetrical with respect to a central plane of said base layer, and
wherein said continuous strips are folded so as to form four parallel branches, with the adjacent branches joined to one another by folds, wherein two central adjacent branches are made of elasticized material and two end branches are made of non-elasticized material.

16. The method according to claim 15, wherein each of said continuous strips comprises a central elasticized stretch and two side stretches made of non-elasticized material, and in that said base layer is made of non-elasticized material.

17. The method according to claim 15, wherein said continuous strips and said base layer are made of non-elasticized material.

18. The method according to claim 15, wherein said continuous strips are folded according to a C-shaped configuration.

19. The method according to claim 15, wherein a line of preferential tearing is provided in a region corresponding to the fold between said central branches.

20. The method according to claim 19, wherein a line of preferential tearing is provided in a region corresponding to the fold between said branches folded to form a C.

21. The method according to claim 15, wherein the two central branches are connected to one another by means of a releasable and refastenable closure device.

22. The method according to claim 19, wherein said branches folded to form a C are connected to one another by means of a releasable and refastenable closure device.

23. The method according to claim 15, wherein micro-hook closure devices are fixed to the branches of said strips opposite to said base layer.

24. A disposable pant-like absorbent sanitary product, comprising an absorbent structure and two side panels, wherein each of said side panels is formed by one half of a closure element obtained by means of a method according to claim 15.

* * * * *